United States Patent
Bamford et al.

(10) Patent No.: US 10,521,644 B2
(45) Date of Patent: Dec. 31, 2019

(54) LAB COLOR SPACE SILVER AND RED IN SITU HYBRIDIZATION BASED TECHNIQUES FOR DETECTING GENES IN TISSUE SAMPLES

(71) Applicant: Ventana Medical Systems, Inc., Tucson, AZ (US)

(72) Inventors: Pascal Bamford, San Diego, CA (US); Srinivas Chukka, San Jose, CA (US); Jim F. Martin, Mountain View, CA (US); Anindya Sarkar, Sunnyvale, CA (US); Olcay Sertel, Sunnyvale, CA (US); Ellen Suzue, Sunnyvale, CA (US); Harshal Varangaonkar, Belmont, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 1324 days.

(21) Appl. No.: 14/372,673

(22) PCT Filed: Jan. 29, 2013

(86) PCT No.: PCT/EP2013/051705
§ 371 (c)(1),
(2) Date: Jul. 16, 2014

(87) PCT Pub. No.: WO2013/113707
PCT Pub. Date: Aug. 8, 2013

(65) Prior Publication Data
US 2014/0377753 A1  Dec. 25, 2014

Related U.S. Application Data

(60) Provisional application No. 61/593,776, filed on Feb. 1, 2012.

(51) Int. Cl.
| | |
|---|---|
| G06K 9/00 | (2006.01) |
| G06T 7/00 | (2017.01) |
| C12Q 1/6813 | (2018.01) |
| G06T 7/90 | (2017.01) |
| G06K 9/46 | (2006.01) |

(52) U.S. Cl.
CPC ....... *G06K 9/00147* (2013.01); *C12Q 1/6813* (2013.01); *G06K 9/4652* (2013.01); *G06T 7/0012* (2013.01); *G06T 7/90* (2017.01); *G06T 2207/10024* (2013.01); *G06T 2207/10056* (2013.01); *G06T 2207/30024* (2013.01)

(58) Field of Classification Search
None
See application file for complete search history.

(56) References Cited

U.S. PATENT DOCUMENTS

| | | |
|---|---|---|
| 5,650,327 A | 7/1997 | Copeland et al. |
| 5,654,200 A | 8/1997 | Copeland et al. |
| 6,296,809 B1 | 10/2001 | Richards et al. |
| 6,352,861 B1 | 3/2002 | Copeland et al. |
| 6,827,901 B2 | 12/2004 | Copeland et al. |
| 6,943,029 B2 | 9/2005 | Copeland et al. |
| 2003/0211630 A1 | 11/2003 | Richards et al. |
| 2004/0052685 A1 | 3/2004 | Richards et al. |
| 2006/0041385 A1 | 2/2006 | Bauer et al. |
| 2008/0299555 A1 | 12/2008 | Nitta et al. |
| 2011/0136130 A1 | 6/2011 | Gniewek et al. |

FOREIGN PATENT DOCUMENTS

| | | |
|---|---|---|
| EP | 2141657 | 1/2010 |
| EP | 2487249 | 8/2012 |
| JP | 2004340738 A | 12/2004 |
| JP | 2008-292256 A | 12/2008 |
| JP | 2011-010621 A | 1/2011 |
| JP | 2011-120070 A | 6/2011 |
| WO | 03033728 A1 | 4/2003 |
| WO | 2005076216 A2 | 8/2005 |
| WO | 2007090683 A1 | 8/2007 |
| WO | 2008031228 A1 | 3/2008 |
| WO | 2008129881 | 10/2008 |
| WO | 2010052543 | 5/2010 |
| WO | 2010088672 A1 | 8/2010 |
| WO | 2011025736 A1 | 3/2011 |
| WO | 2011043077 A1 | 4/2011 |
| WO | 2011049608 A2 | 4/2011 |
| WO | 2014138533 A1 | 9/2014 |

OTHER PUBLICATIONS

Theodosiou, Zenonas, et al. "Evaluation of FISH image analysis system on assessing HER2 amplification in breast carcinoma cases." The Breast 17.1 (2008): 80-84.*
Raimondo, Francesco, et al. "Automated evaluation of Her-2/neu status in breast tissue from fluorescent in situ hybridization images." IEEE Transactions on Image Processing 14.9 (2005): 1288-1299.*
Thomas M. Grogan, et al. "Interpretation Guide Ventana INFORM HER2 Dual ISH DNA Probe Cocktail Assay," 2010, Retrieved from the Internet: URL:http://www.nordiqc.org/ERFA/VENTANA_Guide1010.pdf, retrieved on May 29, 2013.
Young Wha Koh et al. "Dual-color silver-enhanced in situ hybridization for assessing HER2 gene amplification in breast cancer," Modern Pathology, vol. 24, No. 6, Jun. 2011, pp. 794-800.

(Continued)

*Primary Examiner* — G Steven Vanni
(74) *Attorney, Agent, or Firm* — Kilpatrick Townsend & Stockton LLP

(57) ABSTRACT

A computer-based specimen analyzer (10) is configured to detect a level of expression of genes in a cell sample by detecting dots that represent differently stained genes and chromosomes in a cell. The color of the stained genes and the chromosomes is enhanced and filtered to produce a dot mask that defines areas in the image that are genes, chromosomes, or non-genetic material. Metrics are determined for the dots and/or pixels in the image of the cell in areas corresponding to the dots. The metrics are fed to a classifier that separates genes from chromosomes. The results of the classifier are counted to estimate the expression level of genes in the tissue samples.

7 Claims, 7 Drawing Sheets

(56) References Cited

OTHER PUBLICATIONS

Nitta Hiroaki et al. "Development of automated brightfield double In Situ hybridization (BDISH) application for HER2 gene and chromosome 17 centromere (CEN 17) for breast carcinomas and an assay performance comparison to manual dual color HER2 fluorescence In Situ hybridization (FISH)," Diagnostic Pathology, vol. 3, No. 1, Oct. 22, 2008, p. 41.
Hans Netten et al. "FISH and chips: automation of fluorescent dot counting in interphase cell nuclei," Cytometry, vol. 28, No. 1, May 1997, pp. 1-10.
Hans Netten et al. "Fluorescent dot counting in interphase cell nuclei," Bioimaging, vol. 4, No. 2, Jan. 1996, pp. 93-106.
Lerner B. et al. "Automatic signal classification in fluorescence in situ hybridization images," Cytometry, vol. 43, No. 2, Feb. 2001, pp. 87-93.
Defeng Wang et al. "Color quantification for evaluation of stained tissues," Cytometry Part A, vol. 79A, No. 4, Mar. 8, 2011, pp. 311-316.
Pornchai Phukpattaranont et al. "An Automatic Cell Counting Method for a Microscope Tissue Image from Breast Cancer," IFMBE Proceedings (International Federation for Medical and Biological Engineering (3rd Kuala Lumpur International Conference on Biomedical Engineering 2006: Biomed 2006, Dec. 11-14, 2006, Kuala Lumpur, Malaysia, Springer, DE, vol. 15, Jan. 2007, pp. 241-244.
Makio Akimoto et al., Fabrication and Evaluation of Microscopic Colorimeter, Proceedings of 16th Meeting of Japan Society for Laser Microscopy, 1995, pp. 20-24.
INFORM HER2 Dual ISH DNA Probe Cocktail [Online], VENTANA (Registered Trademark), Aug. 23, 2010, [Retrieved on Jun. 26, 2018], p. 1-12, http://www.rochecanada.com/content/dam/roche_canada/en_CA/documents/package_inserts/INFORM HER2 Dual ISH Probe Cocktail-05899826001-PIRevB-En.pdf.
Japanese office action dated Jul. 4, 2018 issued in corresponding Japanese Patent Application No. 2017-088255.
Kurosumi, Masafumi, "Recent Trends of Breast Cancer Therapy Decided by the Results of Immunohistochemistry and in situ Hybridization" Microscopy vol. 44, No. 1 (2009), pp. 30-34.
International Search Report and Written Opinion dated Jun. 17, 2013 in corresponding PCT/EP2013/051705 filed Jan. 29, 2013, pp. 1-14.

\* cited by examiner

LAB COLOR SPACE SILVER AND RED IN SITU HYBRIDIZATION BASED TECHNIQUES FOR DETECTING GENES IN TISSUE SAMPLES

RELATED APPLICATIONS

This patent application is a continuation of International Patent Application No. PCT/EP2013/051705 filed Jan. 29, 2013, which claims priority to and the benefit of U.S. Provisional Application No. 61/593,776, filed Feb. 1, 2012, and entitled "COMPUTER-BASED SYSTEM FOR DETECTING GENES IN TISSUE SAMPLES." The contents of all the aforementioned applications are hereby incorporated by reference in their entirety into this disclosure for all purposes.

TECHNICAL FIELD

The technology disclosed herein relates to computer-based specimen analyzers and in particular computer-based systems for detecting an expression level of genes in tissue samples.

BACKGROUND

Many diseases are associated with the changes that occur in the nuclei of cells. In particular, some types of cancers are associated with the presence of additional genetic material in cells. For example, a certain type of breast cancer is associated with an over abundance (e.g., over expression) of the human epidermal growth factor 2 ("HER2") versus the number of chromosome 17s found in the cell. By detecting the number of HER2 genes versus the number of chromosome 17s in a tissue sample, this particular type of breast cancer can be more readily identified and treatment options can be evaluated.

In a conventional tissue analyzing system, a pathologist uses a microscope to view a tissue sample that has been stained with a "cocktail" mix that includes special gene markers that attach themselves to particular genes, chromosomes or portions thereof. The markers make the attached chromosomes or genes appear as differently colored regions on the stained slide. The pathologist can count or estimate how many objects truly represent the marked genetic material versus extraneous junk in the slide and then make a determination whether a gene is amplified in a particular tissue sample.

SUMMARY

At least some embodiments of the disclosed technology are directed toward building an imaging system for automatically scoring tissue specimens. The system selects candidate nuclei for quantitative analysis. The system automatically counts first in situ hybridization signals and second in situ hybridization signals. A ratio of the count of the first signals to the count of the second signals can be determined.

The system, in some embodiments, includes a computing system that automatically counts the first and second hybridization signals. In certain embodiments, one or both of the first and second hybridization signals are non-fluorescence signals. The non-fluorescence signals can be a silver in situ hybridization signal, a red in situ hybridization signal, or the like. In some embodiments, one signal is a silver in situ hybridization signal ("SISH") that indicates a HER2 gene and another signal is a red in situ hybridization signal that indicates chromosome 17.

In some embodiments, a system evaluates whether a feature of an image should be counted. The system can use at least one image characteristic metric and at least one morphology metric to determine whether a feature corresponds to a gene, protein, chromosome, or other anatomical structure of interest. Image characteristic metrics can include, for example, color, color balance, intensity, or the like. Morphology metrics can include, for example, feature size, feature color, feature orientation, feature shape, relation or distance between features (e.g., adjacent features), relation or distance of a feature relative to another anatomical structure, or the like. Image characteristic metrics, morphology metrics, and other metrics can be used to train a classifier.

A computer-based specimen analyzer, in some embodiments, is configured to detect a level of expression for the features of interest in an image by detecting image features that represent stained features of interest. The color of the stained features is enhanced and filtered to produce a mask that defines areas in the image that are genes, chromosomes, proteins, non-genetic material, or other labeled markers. Metrics can be used to evaluate image features (e.g., dots, pixels, or both) corresponding to the features of interest. The metrics are fed to a classifier that separates different cellular structures.

In some embodiments, a system for detecting an expression level of genes includes memory and a processor. The memory can store a sequence of program instructions. The processor can be programmed to receive a color image of a tissue sample and identify genes and chromosomes that are stained differently in the color image based on the morphology of the cell nuclei. The processor can evaluate the relationship of the identified genes and chromosomes to determine the level of expression of the gene.

The genes or chromosome may appear as dots in the image of the specimen. The processor, in some embodiments, is programmed to identify genes and chromosomes by evaluating at least one of a dot dimension, a dot shape, a dot orientation, a spatial relationship between a plurality of dots, and a spatial relationship between at least one dot and another tissue structure. In certain embodiments, the processor is programmed to measure the dimensions and relative positions of a plurality of dots identified as genes. The processor can also be programmed to measure the dimensions and relative positions of a plurality of dots identified as chromosomes.

The memory can store instructions to evaluate the morphology of the cell nuclei. Stored instructions can be a morphology algorithm. The morphology algorithm can be executed to evaluate, for example, dimensions, positions, form, and structure of tissue or portion thereof. In some embodiments, a gene morphology algorithm is used to evaluate signals corresponding to genes, and a chromosome morphology algorithm is used to evaluate signals corresponding to chromosomes.

At least some embodiments of the disclosed technology include a computer-based system configured to enhance the color of features in a color image of a specimen by converting an image of a cell from an RGB color space to an L*a*b color space and to compute a grayscale image linearly combining the L, a and b values for each pixel. The system can produce a dot mask representing the likely features of interest by filtering the enhanced color image with a number of Difference of Gaussian filters. The filter and associated parameters can be selected to give a strong response for pixels which appear as dots of interest, in size and shape, in the image and minimal response for all other pixels in the image. The computer-based system can be configured to enhance the colors of a wide range of features of interest, including genes, gene products, chromosomes, labels, markers, proteins, or the like.

In some embodiments, an analyzer includes memory for storing a sequence of program instructions and an image of a tissue sample that has been stained such that different features of interest appear differently in the image. The analyzer is configured to execute the instructions in order to enhance the appearance of the features of interest, filter the enhanced image to detect areas that likely represent the different features of interest in the image, and measure one or more metrics for the areas representing the features of interest. In certain embodiments, the metrics include image characteristic metrics or morphology metrics, or both. The metrics can be applied to a classifier that determines whether the areas represent features of interest. The analyzer can count the number of different identified features in the image or portion thereof.

In some embodiments, a computer system can be programmed to automatically determine any areas of interest. Candidate features are selected based on one or more selection criteria, including criteria based on sample morphology (e.g., cell component morphology, cell morphology, tissue morphology, anatomical structure morphology, etc.), tissue characteristics (e.g., density, composition, or the like), spatial parameters (e.g., arrangement of tissue structures, relative positions between tissue structures, etc.), image characteristic parameters, or the like. If the candidate features are nuclei, the selection criteria can include, without limitation, nuclei morphology (e.g., shape, dimensions, composition, etc.), spatial parameters (e.g., position of nuclei in cellular structure, relative position between nuclei, etc.), image characteristics, combinations thereof, or the like. After selecting candidate nuclei, algorithms can be used automatically to perform a quantitative analysis to evaluate HER2 genes/chromosome 17s ratios. A user, in some embodiments, can manually alter the areas of interest based upon visual inspection of the image, if desired. A batch of slides can be analyzed without human intervention, if desired. Areas of interest can be scored. In some embodiments, the user can delete any areas of interest on a slide-by-slide basis. For example, a user may visually determine that an automatically selected field of view is unsuitable for scoring. The user may then delete the selected field of view from further processing.

BRIEF DESCRIPTION OF THE DRAWINGS

The patent or application file contains at least one drawing executed in color. Copies of this patent or patent application publication with color drawings will be provided to the Office upon request and the payment of the necessary fee. The same reference numerals refer to like parts or acts throughout the various views, unless otherwise specified

DETAILED DESCRIPTION

At least some embodiments of the technology disclosed herein relate to computer systems and methods for analyzing cellular material, in particular to systems for detecting over expressed genes in cells. Although exemplary embodiments described herein detect the level of expression (e.g., over or under expression) of the HER2 gene, it will be appreciated that the technology can be used to detect other genes or portions thereof in cells, as well as other features of interest.

Figure 1:
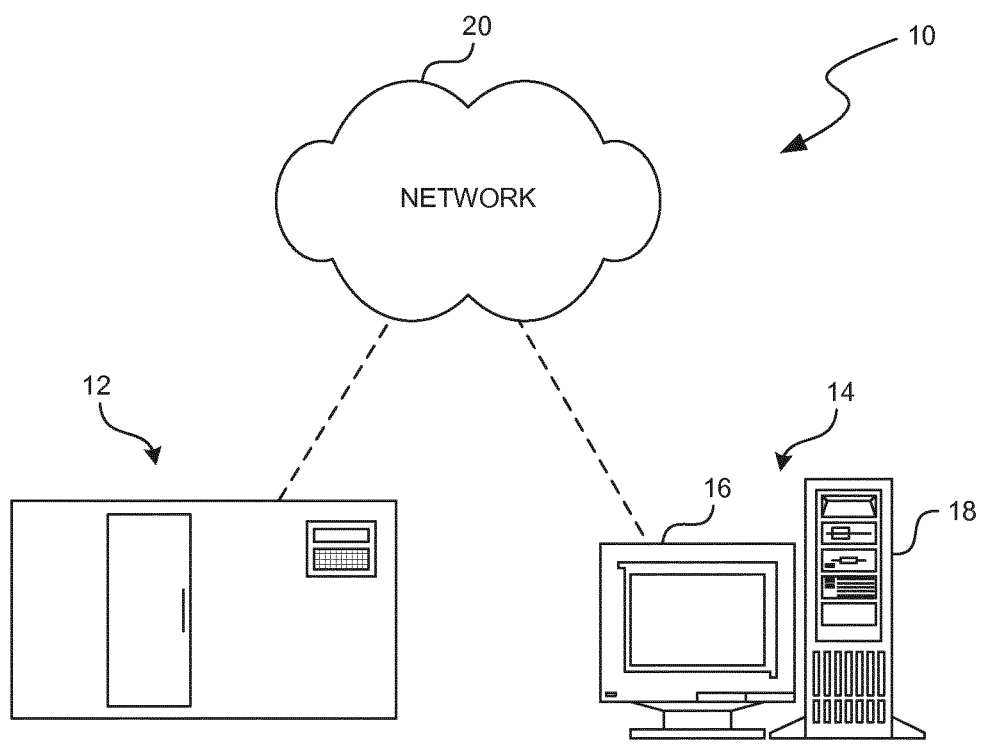
FIG. 1 shows a computer-based system for analyzing specimens in accordance with an embodiment of the disclosed technology.

A computer-based specimen analyzer for analyzing specimens is shown in FIG. 1. An analyzing system 10 includes an imaging apparatus 12 and a computer system 14. Specimen-bearing microscope slides can be loaded into the imaging apparatus 12. The imaging apparatus 12 produces the images of the specimens. The images are sent to a computer system 14 either through a direct connection or via a network 20. The computer system 14 displays the images to a user. The user (e.g., a pathologist, a cellular scientist, a lab technician, or the like) can select one or more areas of the image for evaluation. The computer system 14 can assist the user by scoring the areas with features of interest.

The imaging apparatus 12 can include, without limitation, one or more image capture devices. Image capture devices can include, without limitation, a camera (e.g., an analog camera, a digital camera, etc.), optics (e.g., one or more lenses, sensor focus lens groups, microscope objectives, etc.), imaging sensors (e.g., a charge-coupled device (CCD), a complimentary metal-oxide semiconductor (CMOS) image sensor, or the like), photographic film, or the like. In digital embodiments, the image capture device can include a plurality of lenses that cooperate to prove on-the-fly focusing. A CCD sensor can capture a digital image of the specimen. One method of producing a digital image includes determining a scan area comprising a region of the microscope slide that includes at least a portion of the specimen. The scan area may be divided into a plurality of snapshots. An image can be produced by combining the snapshots. In some embodiments, the imaging apparatus 12 produces a high-resolution image of the entire specimen.

The computer system 14 can include a desktop computer, a laptop computer, a tablet, or the like and can include digital electronic circuitry, firmware, hardware, memory, a computer storage medium, a computer program, a processor (including a programmed processor), or the like. The illustrated computing system 14 of FIG. 1 is a desktop computer with a screen 16 and a tower 18. The tower 18 can store digital images in binary form. The images can also be divided into a matrix of pixels. The pixels can include a digital value of one or more bits, defined by the bit depth. The digital value may represent, for example, energy, brightness, color, intensity, sound, elevation, or a classified value derived through image processing. Non-limiting exemplary digital image formats include, but are not limited to, bit-mapped, joint pictures expert group (JPEG), tagged image file format (TIFF), and graphics interchange format (GIF), as well as other digital data formats.

The network 20 or a direct connection interconnects the imaging apparatus 12 and the computer system 14. The network 20 may include, without limitation, one or more gateways, routers, bridges, combinations thereof, or the like. The network 20 may include one or more servers and one or more websites that are accessible to users and can be used to send and receive information that the computer system 14 can utilize. A server may include, without limitation, one or more associated databases for storing information (e.g., digital images, algorithms, staining protocols, or the like). The network 20 can include, but is not limited to, data networks using the Transmission Control Protocol (TCP), User Datagram Protocol (UDP), Internet Protocol (IP) and other data protocols.

The specimen can be a breast tissue sample processed according to an in situ hybridization ("ISH") protocol. The ISH protocol can provide visualization of specific nucleic acid sequences (e.g., DNA, mRNA, etc.) in frozen tissue sections, fixed/paraffin embedded tissue sections, or other cell preparations by hybridizing complementary strands of nucleotides (e.g., probes) to the sequence of interest. The ISH protocol can include, without limitation, a dual SISH and Red ISH protocol, single Red ISH protocol, single SISH protocol, or the like. To determine a HER2/chromosome 17 ratio, the imaging apparatus 12 captures images that include silver in situ hybridization signals, red in situ hybridization signals, or the like. The tissue is scored based on the signals corresponding to HER2 genes and chromosome 17s to determine the HER2/chromosome 17 ratio. Based on the ratio, the specimen's HER2 gene is determined to be amplified or not amplified. To automatically score the breast tissue sample, candidate nuclei can be selected for quantitative analysis. The computer system 14 automatically counts different features (e.g., HER2 genes, chromosome 17s, etc.) and determines the ratio of the number of features. Additional nuclei can be scored. A diagnosis can be made based, at least in part, on the ratios. Results can be displayed on the screen 16. To evaluate whether the tissue sample (e.g., breast tissue) is a carcinoma, the computer system 14 can assist the user in obtaining information about the selected region by, for example, detecting the amplification of genes by evaluating the ratio of the number of HER2 gene signals to the number of chromosome 17 signals. The term "detecting" as used herein includes quantitative detection or qualitative detection, or both. In certain embodiments, a biological sample comprises a cell or tissue.

The analyzing system 10 can perform the methods and techniques discussed in connection with FIGS. 2-7. Components and features of the analyzing system 10 can be mixed and matched with other components and features of the systems of FIGS. 2-5 and 7.

Figure 2:
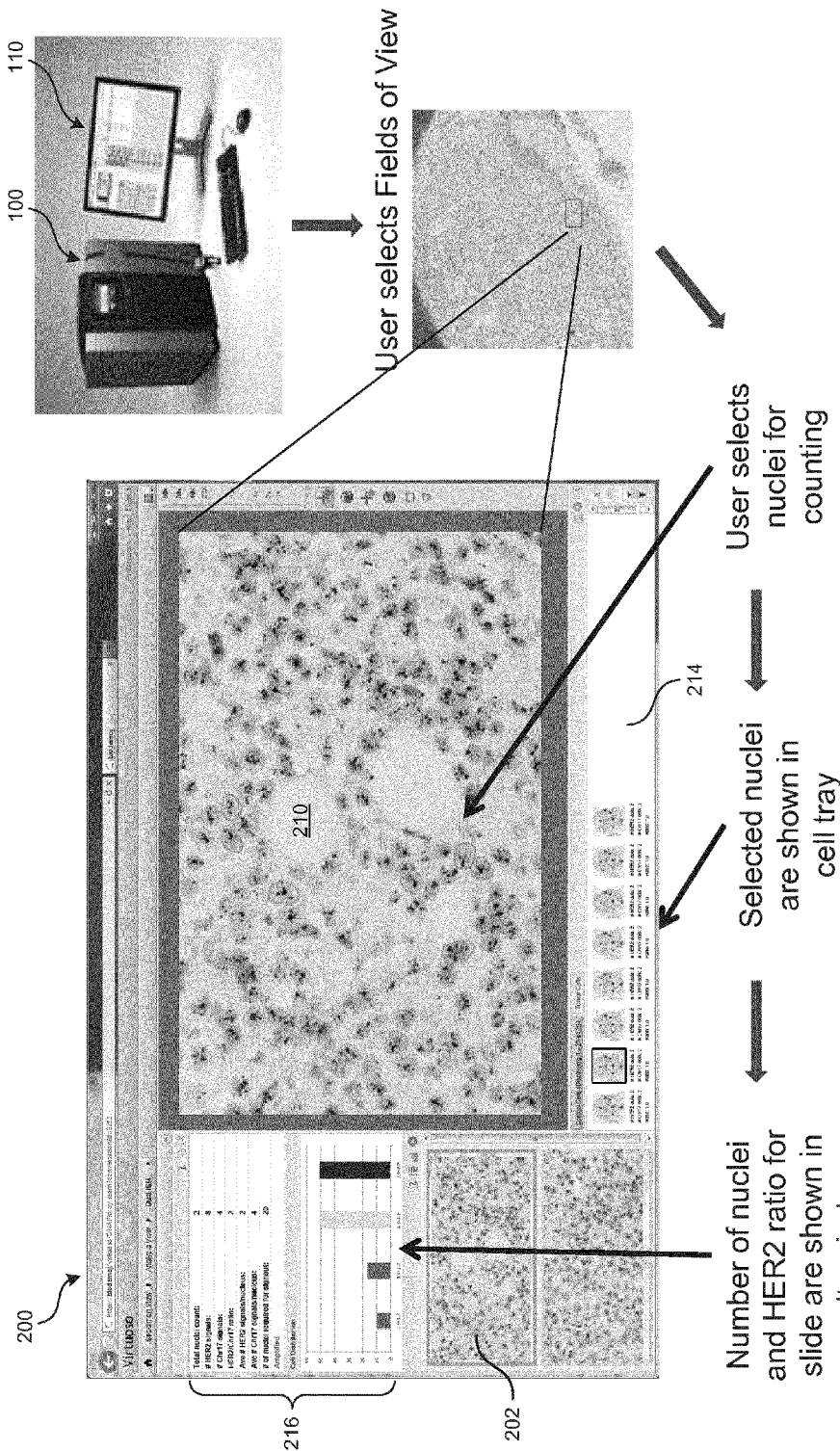
FIG. 2 shows an illustrative user-interface ("UI") screen that allows a user to view selected cell nuclei and the results of a cellular analysis performed by a computer system in accordance with an embodiment of the disclosed technology.

FIG. 2 illustrates a portion of a user interface (UI) screen that allows a user to interact with a computer-based specimen analyzer that analyzes cells in accordance with the disclosed technology. A specimen in the form of a tissue sample can be prepared by staining using a cocktail assay, mounting the stained tissue on a slide, and imaging the slide with a high-resolution imaging apparatus that may be associated with a computer system 100 or may be a separate component or system. A color digital image of the tissue sample is stored in a local or remote computer-readable storage media (hard disk, solid state memory or the like) and displayed on a display 110.

An illustrative user interface 200 created by the computer system 100 is shown on the display 110. The UI 200 includes a window 202 that shows the image of the tissue sample or a portion thereof. A user uses a selection tool (mouse, joystick, icon such as a lasso tool or one or more key strokes or other mechanism) to select a portion of the tissue displayed in the image as a field of view ("FOV"). An enlarged view of the tissue within the selected field of view is shown in a window 210. The user can then select individual cells/nuclei with a selection tool for analysis. The illustrated user-selected boundaries (illustrated in green) generally correspond to nuclear membranes. Portions of the image within the boundaries can be analyzed. Alternatively, the computer system can employ a cell/nuclei detection algorithm to select a number of cells. The detection algorithm can determine boundaries based on, for example, image characteristic parameters, tissue morphology, tissue characteristics, spatial parameters, combinations thereof, or the like. As will be appreciated by those skilled in the art, the genetic material detected by the disclosed technology appears in the nucleus of cells. Therefore the terms "cell" and "nucleus" and their plural forms are deemed to be synonymous for purposes of the present disclosure. Selected cells are highlighted in the window 210 by outlining the cell with a color that can be seen, by shading the area of the cell, or other means.

Color images of individual cells that are selected for analysis are displayed in a cell tray 214 at the bottom of the UI 200. If the user manually identifies cells, then an image of each such identified cell can be placed in the cell tray 214. If the computer system 100 automatically identifies the cells, then an image of each such automatically identified cell can be included in the cell tray 214. Alternatively, the user can manually confirm the selection of one or more of the automatically identified cells to be included in the cell tray 214.

The user interface 200 also includes one or more windows 216 that display the results of an analysis computed for the cell nuclei that are included in the cell tray 214. In one embodiment, the analysis determines the ratio of the number of HER2 genes versus the number of chromosome 17s found for each such cell identified in the FOV. As indicated above, the ratio may be indicative of certain types of cancer. The results of the HER2/chromosome 17 ratio determined for each identified cell and the slide as a whole are stored in a record for the corresponding slide. A user can conveniently view the HER2/chromosome 17 ratio without visually counting the HER2 genes and chromosome 17s, which can be very time consuming and tedious, and therefore error-prone. The automated scoring process can reduce the time it takes to diagnose and thus increase laboratory throughput. Additionally, the automated process can provide consistent and reliable scoring to enhance interpretation accuracy.

In one embodiment, each slide is marked with a bar code, machine-readable code (e.g., a one- or multidimensional bar code or infoglyph, an RFID tag, a Bragg-diffraction grating, a magnetic stripe, or a nanobarcode), or some other type of electronically detectable identifier in order to, for example, match the results of the analysis to a particular slide. If the slide is reinserted into an imaging apparatus (including a slide viewer) of the computer system, the determined statistics can be recalled from the computer-readable storage media and displayed for the user. In addition or alternatively, the record of the analysis performed for the tissue in the slide can be transmitted over a computer communication link (e.g., the Internet) to a remote computer system for viewing, storage or analysis. Such records can be combined with the analysis of other tissue samples for a variety of purposes, such as medical research, etc. The computer may also produce one or more reports concerning the tissue analysis for inclusion in a patient's records. Once the analysis is performed on the cells that are included in the cell tray 214, the user may quit the analysis or may select another FOV in the image of the tissue sample.

Figure 3:
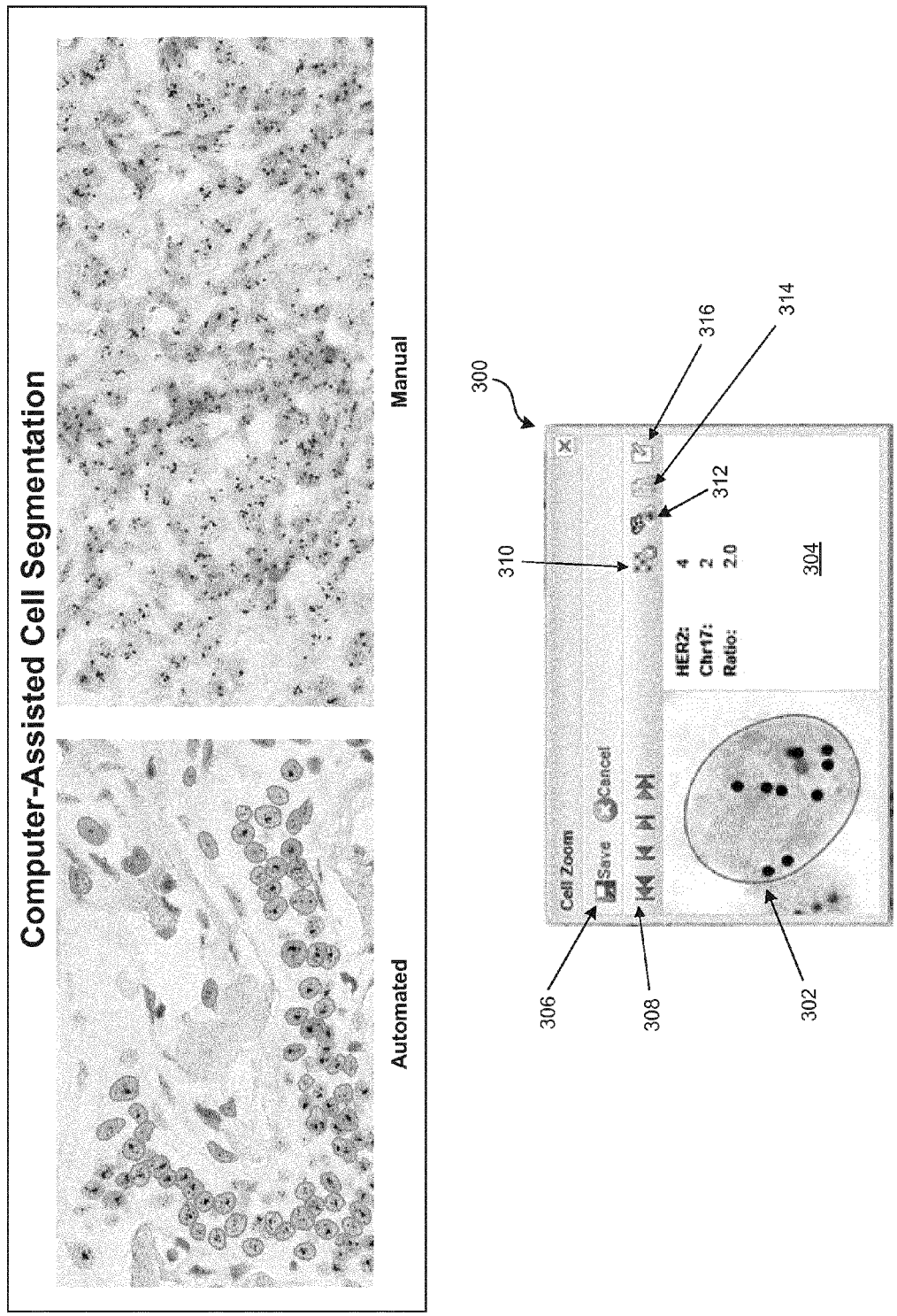
FIG. 3 illustrates a user interface window in which a cell is displayed along with detected HER2 genes and chromosome 17s and the statistics computed for the cell that are produced in accordance with an embodiment of the disclosed technology.

FIG. 3 illustrates a representative window 300 produced by the UI upon selecting an individual cell in the cell tray 214. The window 300 includes an image 302 of the selected cell along with a display 304 that indicates the number of HER2 genes and chromosome 17s detected in the cell. A user can override the number of automatically detected HER2 genes or chromosome 17s if desired. A number of controls 306 allow the user to save the results for the cell or to cancel. Controls 308 allow the user to scroll through each of the cells in the cell tray. Controls 308 include a rewind button to return to the first cell in the cell tray, a back button to allow a user to return to the previous cell in the cell tray, a next cell button to allow a user to advance to the next cell in the cell tray, and a fast forward button to allow a user to advance to the last cell in the cell tray. A button 310 allows a user to delete the cell shown from the cell tray. A button 312 allows the user to toggle an outline of the cell boundary on and off as well as images of black and red dots indicating the location of detected HER2 genes and chromosome 17s, respectively, within the cell boundary. A button 314 allows the user to include the statistics that have been computed for the cell in a report for the slide. Finally, a button 316 allows a user to override the computer-determined statistics for any particular cell and enter their own estimate of the number of HER2 genes and chromosome 17s for the cell.

Figure 4:
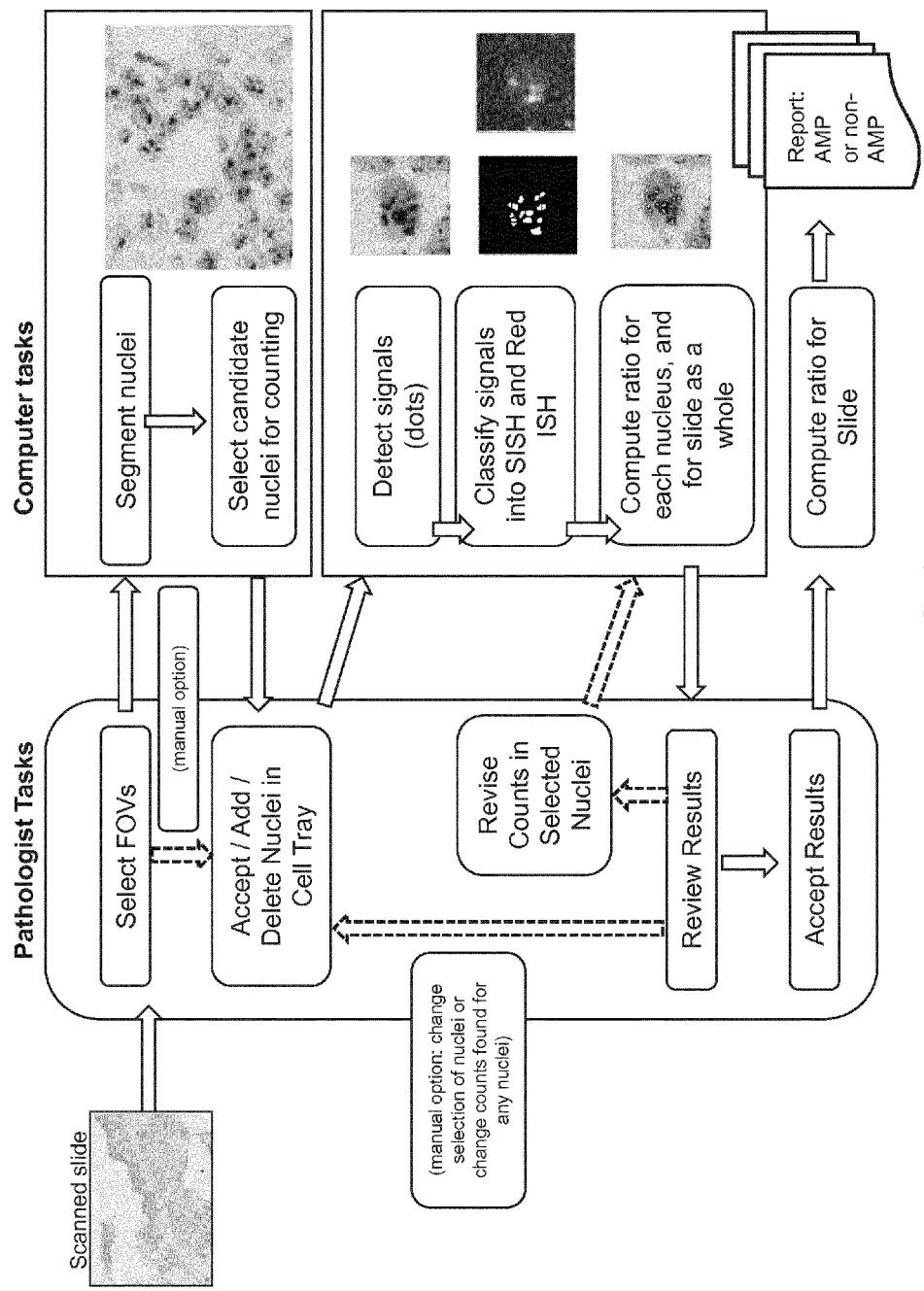
FIG. 4 shows a workflow diagram of a computer-implemented method for analyzing cell nuclear material in accordance with an embodiment of the disclosed technology.
Figure 5:
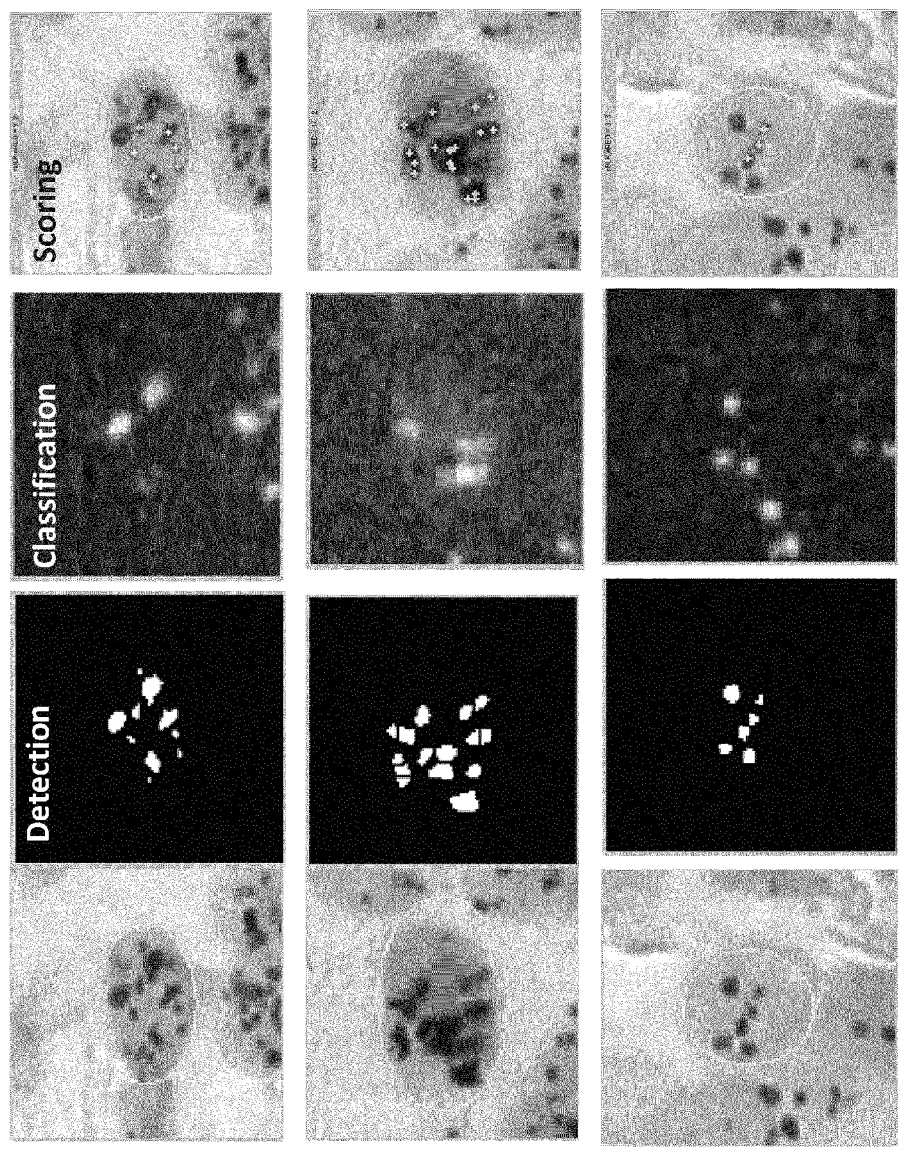
FIG. 5 illustrates a number of selected cells, dot mask images created from the cells, and detected genetic material in accordance with an embodiment of the disclosed technology.

FIG. 4 shows one representative workflow diagram of a method for analyzing cells in accordance with the disclosed technology. Although the acts shown are described as being performed in a particular order for ease of explanation, it will be appreciated that the order of acts may be changed, acts may be omitted, or additional acts performed while still obtaining the functionality described.

In one embodiment, the computer systems 14, 100 include one or more processors that are programmed with a series of computer-executable instructions that are stored on a non-transitory, computer readable media. When executed, the instructions cause the one or more processors of the computer system to receive an indication of one or more FOVs from a user. In one embodiment, the computer system then executes instructions that cause one or more processors to segment or identify the boundaries of the cell nuclei contained in the selected FOV. In one embodiment, the computer system 100 executes instructions to automatically identify the boundaries of the cell nuclei. In another embodiment, the computer systems execute instructions to receive an indication of the cell nuclei from a user using the selection tool. In one embodiment, an image of each cell nuclei identified is placed into the cell tray within the user interface 200.

Once the desired number of cells is selected for analysis in the cell tray, the computer system executes instructions to detect signals (e.g., dots) within each identified cell nucleus. In one embodiment, dots are first identified by converting the color image of a cell to a monochromatic image. In one embodiment, the monochromatic image is created by first transforming the color space of the color image of the cell from an RGB color space to an L*a*b color space. In the L*a*b color space, the "L" channel represents the brightness of a pixel, the "a" channel reflects the red and green components of a pixel, and the "b" channel represents the blue and yellow components of a pixel. A new image is then created that emphasizes the red and black colors in the image which is obtained by linearly combining the "L," "a" and "b" values at each pixel location.

Dots are detected in the red and black-enhanced image by running the enhanced image though a number of filters. In one embodiment, the filters are Difference of Gaussian ("DOG") filters where each filter size is selected based on the expected size of the dots/clumps of dots to be detected. In one embodiment, the size of the DOG filters ranges from about 0.05 microns to about 5 microns. The results from each pass though the DOG filters are combined to create a filtered gray scale image that is used as a mask to represent the stained nuclear material and some "junk" within each cell.

The combined gray scale image is then binarized using, for example, an adaptive thresholding technique based on the Otsu method to produce a dot mask image where everything outside the dot has one binary value (e.g., a logic 0) and everything inside a dot has an opposite binary value (e.g., a logic 1).

Once the dot mask image has been created, it is used with a classifier to remove any dots associated with junk and to leave the dots that represent HER2 genes and chromosome 17s. In one embodiment, a linear binary classifier is used—although other classifiers are equally applicable. In the first stage using the classifier, the computer system executes instructions to prune out dots with weak DOG responses based on a histogram of responses determined for each of the cells analyzed.

In a second stage, the bold red dots are separated from the faint red dots and the black dots are separated from the dark blue dots by analyzing the color of the RGB image of the tissue at pixel locations that correspond to the area within each of the dots in the dot mask image. The result is a set of only red and black dots. The remainder of the dots are considered junk and are removed. Dots and dot blobs are then extracted using a connected component analysis.

To determine if a dot represents a HER2 gene or a chromosome 17, multiple metrics of the dots (including dot blobs) are measured and analyzed. These metrics include dot size, color, orientation, shape, response of the multiple difference of Gaussian filters, relation or distance between adjacent dots, and a number of other factors that can be measured by the computer. The metrics are then inputted into the classifier. The classifier has previously been trained on a training set of data that have been positively identified as representing either a HER2 gene or a chromosome 17 by a trained pathologist, cellular scientist, or other individual or machine—including computer models of these nuclear features.

In one embodiment the classifier has been trained on a set of training slides that contain a range of dot variability and the linear margin binary classifier model has been taught for each stage. The resulting model, parameterized by a discriminant hyperplane, divides the feature space into two labeled regions that define either a HER2 gene or a chromosome 17.

Once the classifier has been trained, the metrics measured for the unknown dots in the image are applied to the classifier. The classifier can then indicate what type of dot (e.g., HER2 gene or chromosome 17) is represented.

Once the dots have been classified, they are counted by the computer system. If the computer system determines that the size of the dot is on the scale of a nominal single dot size, then the dot is counted as either a HER2 dot or a chromosome 17 dot, as labeled by the classifier. If the dot is larger than the nominal single dot size then the computer system determines the area of the cluster and divides it by the area of a nominal dot to determine how many dots are likely included in the dot cluster. The closeness of the dots classified as HER2 and chromosome 17 is used in the counting algorithm.

Once the dots have been classified and counted, the results are tallied on a per cell basis and on a per FOV basis. A ratio of the dot types is calculated and displayed for each cell and slide as a whole. Based on the ratio, the expression level can be determined to be an over-expression, under-expression, etc. In one embodiment, a tissue sample is identified as being over-expressed if the ratio of HER2 genes to chromosome 17s in the tissue sample exceeds, for example, 2.2. Such over-expressed HER2 genes may indicate carcinoma.

The computer systems 14, 100 can execute a morphology algorithm to evaluate one or more features in the image. A gene morphology algorithm can evaluate signals in the color image by, for example, measuring one or more of the dot dimensions, evaluating a dot shape, evaluating a dot orientation, evaluating the spatial relationship between a plurality of dots, and evaluating the spatial relationship between at least one dot and another anatomical structure of the tissue sample. The output can be sent to a classifier that determines whether the signal represents a gene. Other types of morphology algorithms can be used to identify other features of the tissue. The outputs can be sent to a classifier.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable microprocessor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode) display, or OLED (organic light emitting diode) display, for displaying information to the user and a keyboard and a pointing device, e.g., a mouse or a trackball, by which the user can provide input to the computer. In some implementations, a touch screen can be used to display information and receive input from a user. Other kinds of devices can be used to provide for interaction with a user as well; for example, feedback provided to the user can be in any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks). For example, the network 20 of FIG. 1 can include one or more local area networks.

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Figure 6:
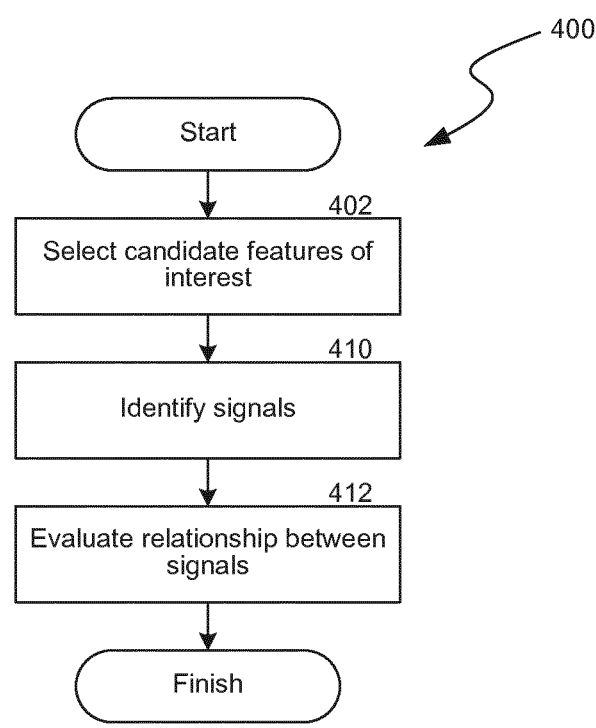
FIG. 6 is a flow diagram of a method for analyzing a specimen in accordance with an embodiment of the disclosed technology.

FIG. 6 is a flow diagram 400 of a method for analyzing a specimen. At 402, candidate features in an image of a tissue specimen are selected. The candidate features can be selected by a computer system or a user.

At 410, signals are identified. In the HER2/chromosome 17 ratio analysis, a first in situ hybridization signal (e.g., a dot) indicates a HER2 gene and a second in situ hybridization signal (e.g., a dot) indicates chromosome 17. These different hybridization signals can be counted.

At 412, the relationship between the signals is evaluated. In certain embodiments, the ratio of the counted signals is determined. Other types of relationships between the signals can be evaluated.

The method 400 can be repeated any number of times to evaluate any desired areas of interest. The computer system can determine the area of interest based on metrics, including image characteristic metrics, morphology metrics, combinations thereof, or the like. For an area or areas of interest, an aggregate score, an average score, or other type of score can be determined. Based at least in part on the score, a pathologist can make a diagnosis.

Figure 7:
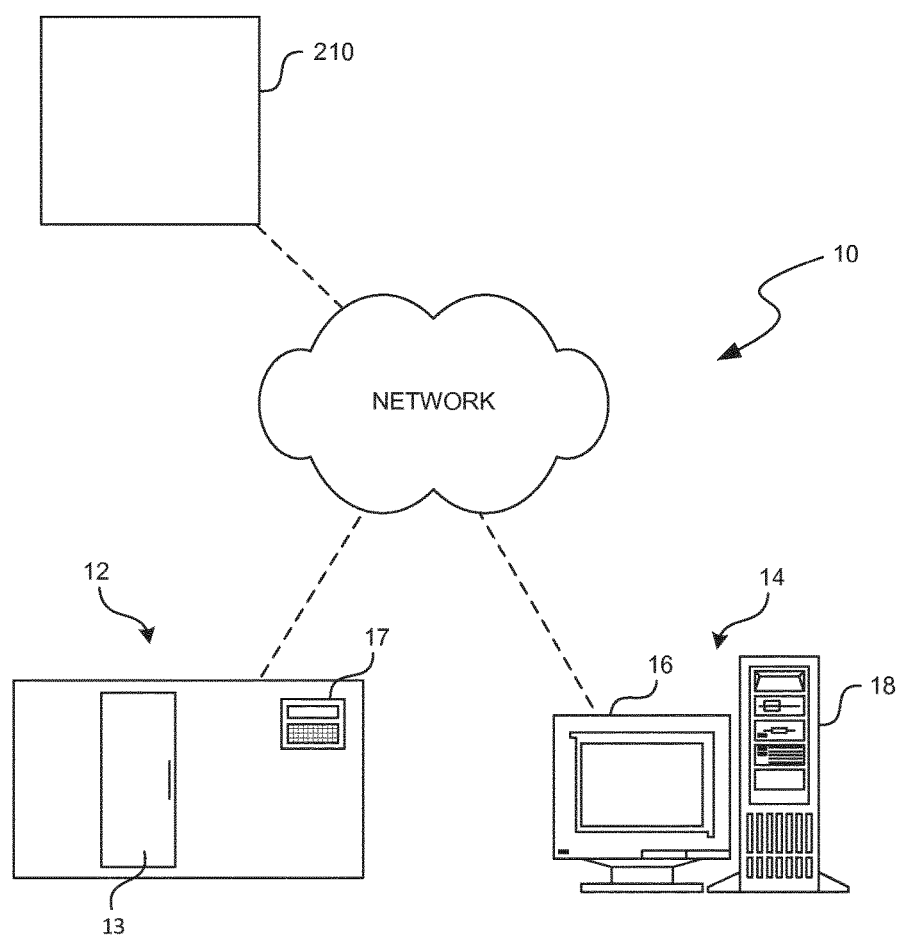
FIG. 7 shows a system for preparing and analyzing specimens in accordance with an embodiment of the disclosed technology.

FIG. 7 shows an analyzing system 10 capable of performing tissue preparation through scoring. A specimen processing apparatus 210 can perform one or more preparation processes on a specimen. The preparation process can include, without limitation, deparaffinizing a specimen, conditioning a specimen (e.g., cell conditioning), staining a specimen, performing antigen retrieval, performing immunohistochemistry staining (including labeling) or other reactions, and/or performing in situ hybridization (e.g., SISH, FISH, etc.) staining (including labeling) or other reactions, as well as other processes for preparing specimens for microscopy, microanalyses, mass spectrometric methods, or other analytical methods.

A specimen can include a tissue sample. The sample of tissue can be any liquid, semi-solid or solid substance (or material) in or on which a target can be present. In particular, a tissue sample can be a biological sample or a tissue sample obtained from a biological tissue. The tissue can be a collection of interconnected cells that perform a similar function within an organism. In some examples, the biological sample is obtained from an animal subject, such as a human subject. A biological sample can be any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In certain examples, a sample is a quality control sample, such as one of the disclosed cell pellet section samples. In other examples, a sample is a test sample. For example, a test sample is a cell, a tissue or cell pellet section prepared from a biological sample obtained from a subject. In an example, the subject is one that is at risk or has acquired a particular condition or disease. In some embodiments, the specimen is breast tissue.

The processing apparatus 210 can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized using appropriate deparaffinizing fluid(s). After the waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus 210 can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or nonaqueous-based antigen retrieval solutions, antigen recovering buffers, etc.), or the like.

Probes can be an isolated nucleic acid or an isolated synthetic oligonucleotide, attached to a detectable label or reporter molecule. Labels can include radioactive isotopes, enzyme substrates, co-factors, ligands, chemiluminescent or fluorescent agents, haptens, and enzymes. For example, probes can include, without limitation, a hapten-labeled specific binding moiety, a DNA probe (e.g., DNP-labeled DNA probe), a nitroaryl compound, dinitrophenol, an electron-deficient aromatic compound, a probe hybridization solution, or other type of ISH probes. ISH can involve a labeled complementary DNA or RNA strand (i.e., probe) to localize a specific DNA or RNA sequence in a portion or section of tissue (in situ), or, if the tissue is small enough, in the entire tissue (whole mount ISH).

In some embodiments, a cocktail assay applied by the processing apparatus 210 includes different reagents. For example, one cocktail assay includes the ULTRAVIEW SISH Detection Kit (Ventana Medical Systems, Inc., p/n 780-001), the INFORM HER2 DNA Probe (Ventana Medical Systems, Inc., p/n 780-4332), the Rabbit Anti-DNP Antibody (Ventana Medical Systems, Inc., p/n 780-4335), the Rabbit Anti-HER2 (4B5) Antibody (Ventana Medical Systems, Inc., p/n 800-2996), the ULTRAVIEW Universal Alkaline Phosphatase Red Detection Kit (Ventana Medical Systems, Inc., p/n 760-501), the silver wash (Ventana Medical Systems, Inc., p/n 780-002), and/or the INFORM Chromosome 17 Probe (Ventana Medical Systems, Inc., p/n 780-4331). Another cocktail assay is the INFORM HER2 Dual ISH DNA Probe sold by (Ventana Medical Systems, Inc.), which includes the INFORM HER2 Dual ISH DNA Probe Cocktail (Ventana Medical Systems, Inc., p/n 800-4422), the HybReady (Ventana Medical Systems, Inc., p/n 780-4409), the ultraView SISH DNP Detection Kit (Ventana Medical Systems, Inc., p/n 800-098), the ultraView Red ISH DIG Detection Kit (Ventana Medical Systems, Inc., p/n 800-505), the ultraView Siler Wash II (Ventana Medical Systems, Inc., p/n 780-003), and/or the HER2 Dual ISH 3-in-1 Xenograft Slides (Ventana Medical Systems, Inc., p/n 783-4332). Other cocktail assays can be used. Cocktail assays can be used to quantitatively detect amplification of the HER2 gene via two color chromogenic ISH in formalin-fixed, paraffin-embedded tissue specimens of human breast cancer and gastric cancer, including the gastro-oesophagal junction and can be an aid in the assessment of patients for whom Herceptin (trastuzumab) may be a treatment option. In yet other protocols, the cocktail assay is the VENTANA HER2 DNA Probe Assay sold by Ventana Medical Systems, Inc., p/n 800-4422. U.S. patent application Ser. No. 11/809,024 (corresponding to U.S. Patent Publication No. 2008/0299555) entitled MULTICOLOR CHROMOGENIC DETECTION OF BIOMAKERS and U.S. patent application Ser. No. 11/809,024 (corresponding to U.S. Patent Publication No. 2011/0136130) entitled METHOD FOR CHROMOGENIC DETECTION OF TWO OR MORE TARGET MOLECULES IN A SINGLE SAMPLE disclose substances, protocols, and specimen processing techniques and are incorporated by reference in their entireties.

The specimen processing apparatus 210 can be an automated apparatus, such as the BENCHMARK XT instrument and SYMPHONY instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Alternatively, specimens can be manually processed.

After the specimens are processed, a user can transport specimen-bearing slides to the imaging apparatus 12. A door 13 can be opened to load the apparatus 12. An input device 17 (illustrated as a control panel) is used to operate the apparatus 12. The imaging apparatus 12 can be a brightfield imager or other type of slide scanner. One brightfield imager is the iScan Coreo™ brightfield scanner sold by Ventana Medical Systems, Inc. In automated embodiments, the imaging apparatus 12 is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application No. 61/533,114, filed on Sep. 9, 2011, entitled IMAGING SYSTEMS, CASSETTES, AND METHODS OF USING THE SAME. International Patent Application No. PCT/US2010/002772 and U.S. Patent Application No. 61/533,114 are incorporated by reference in their entities. In other embodiments, the imaging apparatus 12 includes a digital camera coupled to a microscope.

A user can use the computing system 14 of FIG. 7 to control the processing apparatus 210 and select an image from a database of digitized slide images. The user can select one or more areas of interest for analysis. The computer system 14 automatically counts signals in each area of interest to determine whether sufficient number of SISH signal and red ISH signals are present for a sufficiently accurate estimation of the HER2/chromosome 17 ratio. The results are displayed to the user. If the user decides to proceed with an analysis of any specific area of interest, the user has the option of either selecting the set of nuclei to be included in the estimate or using an algorithm to automatically identify candidate nuclei. The user can delete any candidate nuclei identified using by the algorithm. In some embodiments, an entire image of the specimen is analyzed for qualitative analysis. An overall count can be determined for the specimen. The user can then determine whether to focus the analysis on certain areas of specimen.

Each of the selected nuclei are examined for SISH and Red ISH signals. The ratio of SISH to Red ISH is estimated for each nucleus. The SISH and Red ISH signals found in the selected nuclei are combined to form a HER2/chromosome 17 ratio for the entire area of interest. The user can accept the result as an official annotation for that sample. Alternatively, the user can discard the result and restart the process based on, for example, a different set of nuclei, a new area of interest, or the like. Throughout the process, results in the form of numbers or images are displayed to the user. Based on the results, the user can intervene or continue. In addition to this interactive or user-assisted approach, the computer system 14 can automatically analyze each area of without any human intervention. The user can control operation of the specimen processing apparatus 210 based on the analysis to improve subsequent specimen processing.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

The invention claimed is:

1. A method for automated scoring of a tissue specimen, comprising:
   a) applying a first in situ hybridization probe and a second in situ hybridization probe to the tissue specimen, wherein each of the first in situ hybridization probe and the second in situ hybridization probe comprises a silver in situ hybridization probe or a red in situ hybridization probe;
   b) subsequently obtaining a digital image of the tissue specimen;
   c) enhancing the digital image by converting the digital image from an RGB color space to an L*a*b* color space;
   d) selecting a field of view;
   e) employing an automatic cell-detection and/or nucleus-detection algorithm to select candidate nuclei within the field of view in the digital image for quantitative analysis;
   f) automatically counting in the candidate nuclei a first signal from the first in situ hybridization probe and a second signal from the second in situ hybridization probe; and
   g) estimating a ratio of the counts of the first and second signal.

2. The method of claim 1, further comprising repeating steps e), f), and g) for a second field of view in the digital image.

3. The method of claim 1, wherein the tissue specimen comprises a breast cancer specimen and wherein the method further comprises a step h) reporting the ratio.

4. The method of claim 1, wherein step d) is performed automatically.

5. The method of claim 4, wherein step e) is performed automatically.

6. The method of claim 1, further comprising h) displaying an image of the field of view and the ratio.

7. The method of claim 1, wherein step d) comprises analyzing a color balance of signals from the first and second in situ hybridization probes and selecting the field of view if the color balance meets a predetermined criteria.

* * * * *